United States Patent [19]

Gatechair et al.

[11] Patent Number: 5,290,888
[45] Date of Patent: Mar. 1, 1994

[54] PROCESS FOR STABILIZING ETHYLENICALLY UNSATURATED COMPOUNDS AND STABILIZED MONOMER COMPOSITIONS

[75] Inventors: Leslie R. Gatechair, Katonah, N.Y.; James L. Hyun, Danbury; Peter J. Schirmann, Fairfield, both of Conn.

[73] Assignee: Ciba-Geigy Corporation, Ardsley, N.Y.

[21] Appl. No.: 956,437

[22] Filed: Oct. 2, 1992

Related U.S. Application Data

[63] Continuation of Ser. No. 809,218, Dec. 16, 1991, abandoned, which is a continuation of Ser. No. 556,240, Jul. 20, 1990, abandoned.

[51] Int. Cl.$^5$ ............ C08F 2/40; C07D 251/42; C07D 211/94
[52] U.S. Cl. ........................ 526/83; 544/194; 544/195; 544/214; 544/215; 546/17; 546/188; 546/217; 546/218; 546/223; 546/225; 546/242; 546/244; 546/25
[58] Field of Search .......... 544/194, 195, 214, 215; 546/17, 188, 217, 218, 223, 225, 242, 244, 25; 526/83

[56] References Cited

U.S. PATENT DOCUMENTS

| | | | |
|---|---|---|---|
| 3,148,225 | 9/1964 | Albert | 260/669 |
| 3,222,334 | 12/1965 | Demme | 260/84.7 |
| 3,408,422 | 10/1968 | May | 260/837 |
| 3,697,470 | 10/1972 | Haines et al. | 260/29.7 |
| 3,878,181 | 4/1975 | Mayer-Mader et al. | 260/92.3 |
| 4,409,408 | 10/1983 | Miller | 585/4 |
| 4,434,307 | 2/1984 | Miller | 585/4 |
| 4,668,721 | 5/1987 | Seltzer et al. | 524/95 |
| 4,670,131 | 2/1987 | Ferrell | 585/950 |
| 4,691,015 | 9/1987 | Behrens et al. | 544/188 |
| 4,782,105 | 11/1988 | Ravichandran et al. | 524/236 |
| 4,798,889 | 1/1989 | Plueddemann et al. | 556/401 |
| 4,808,645 | 2/1989 | Ravichandran et al. | 546/25 |

FOREIGN PATENT DOCUMENTS

| | | |
|---|---|---|
| 0178168 | 4/1986 | European Pat. Off. |
| 2113246 | 9/1975 | Fed. Rep. of Germany |
| 6036501 | 2/1985 | Japan |
| 1139722 | 2/1985 | U.S.S.R. |
| 1127127 | 10/1968 | United Kingdom |

OTHER PUBLICATIONS

Yozo Miura et al, Die Makromolekulare Chemie, 160, 243–249, 1972.
Ziyi Zhang et al., CA 106 #1202635, 1987.
Y. Miura et al., Makromol Chem. 160, 243 (1972).
Chem. Abst. 107, 33321r (1987).
Yozo et al; Chemical Abstract vol. 87, 1973, 4597h.
Ziyi et al: Chemical Abstract vol. 106, 1987, 120263S.
Ramnathan et al; Chemical Abstract vol. 106, 1987, 33321r.

*Primary Examiner*—John M. Ford
*Assistant Examiner*—Y. N. Gupta
*Attorney, Agent, or Firm*—Luther A. R. Hall

[57] ABSTRACT

A process for stabilizing an ethylenically unsaturated monomer or oligomer from premature polymerization is disclosed whereby a stabilizing amount of an N-hydroxy substituted hindered amine is added to said polymerizable monomer or oligomer. The ethylenically unsaturated monomer or oligomer encompass vinyl monomers or oligomers bearing at least one polymerizable moiety. The N-hydroxy substituted hindered amine inhibits premature polymerization in the liquid and/or vapor phase.

12 Claims, No Drawings

PROCESS FOR STABILIZING ETHYLENICALLY UNSATURATED COMPOUNDS AND STABILIZED MONOMER COMPOSITIONS

This is a continuation of application Ser. No. 07/809,218, filed on Dec. 16, 1991, now abandoned, which is a continuation of application Ser. No. 556,240, filed on Jul. 20, 1990, now abandoned.

The instant invention pertains to a process for stabilizing an ethylenically unsaturated monomer or oligomer from premature polymerization in the liquid and/or vapor phase by adding thereto a stabilizing amount of an N-hydroxy substituted hindered amine.

BACKGROUND OF THE INVENTION

The ethylenically unsaturated compounds which can be polymerized by free radical initiation are commonly called monomers. They constitute a major class of industrial chemicals. Because of the presence of the polymerizable double bond, the widespread sources of initiating radicals from peroxides, light and/or thermal generation, such monomers are prone to undesirable and premature polymerization at various stages during their manufacture, purification, storage, shipping, blending and use. Protection of such monomers from such premature polymerization is needed up to the point where polymerization is actually desired. If premature polymerization does occur, the monomer may suffer contamination by polymer, troublesome increase in viscosity, gelation and/or loss of reactivity. Fouling of distillation equipment including heat exchanger surfaces, storage vessels, transfer lines, pumps, shipping containers and application equipment can occur with ensuing costs of cleaning, downtime, loss of material and unnecessary labor costs. A particularly difficult situation is the preparation of polyol acrylates from polyols and acrylic acid since prolonged heating periods are required to complete the esterification. Premature polymerization can also constitute a safety hazard since uncontrolled exothermic polymerization can cause ruptured vessels, atmospheric contamination, and in extreme cases, explosions and fires. Deterioration of monomers in shipping and storage may also make necessary the use of costly refrigerated shipping and storage facilities.

A further problem is that of undesired polymerization of adventitious monomers, that is, radically-polymerizable unsaturated monomers which occur in commercial products such as hydrocarbon fuels and refinery streams. In these cases, polymerization accompanied by the incorporation of oxygen moieties leads to gum and sludge deposits which can foul carburators, engines, fuel tanks or fuel lines. In refineries, the adventitious monomers in hydrocarbon streams such as cracking products can foul pipelines, valves, pumps, heat exchangers, stills and storage vessels.

Another problem in regard to undesired polymerization of free radical polymerizable monomers is the case of polymerizations which are intentional, but which must be prevented from going too far. For example, the quality of poly(vinyl chloride) suspension polymer and of synthetic rubber made from olefins and dienes is superior (i.e. better molecular weight distribution, stability, and processing properties) if the polymerization is stopped short of complete consumption of the monomers. It is also desirable to have available in a plant conducting vinyl polymerization reactions some rapid and efficient means for stopping a runaway polymerization if other means such as cooling should fail.

It is known that the addition of certain compounds to monomers can retard or even prevent their undesired polymerization, and that when polymerization of the monomer is desired, the inhibitor can be removed or overridden by a deliberately-added polymerization initiator. Various aromatic compounds have been used as such inhibitors in the prior art. Typical ones are hydroquinone, monomethyl ether of hydroquinone (MEHQ), tert-butylphenols, phenothiazine, phenylenediamines and benzoquinones. These are usually used at a level of 50 to 1000 ppm. These inhibitors are not totally effective and even with such inhibitors present, it is often advisable to store such inhibited monomers in a cool place and for limited periods of time. Moreover, these aromatic inhibitors are a cause of serious discoloration problems in the monomers and in polymers deliberately prepared from such monomers. Typically these aromatic inhibitors produce quinoidal chromophoric groups with very high visible light absorbance. The use of stable nitroxyl radicals as inhibitors also leads to discoloration since such compounds are themselves highly colored, usually bright red.

In order to overcome these color problems, a diligent search was made to find alternative inhibitors which are both effective and not discoloring. This search led to the N,N-dialkylhydroxylamines and the N,N-diaralkylhydroxylamines. Some typical references are cited infra.

U.S. Pat. Nos. 3,222,334 and 3,878,181 disclose the use of N,N-dialkylhydroxylamines such as N,N-diethylhydroxylamine as short-stopping agents for emulsion polymerizations of butadiene/styrene rubber and chloroprene.

U.S. Pat. Nos. 3,148,225 and 3,697,470 disclose the use of N,N-dialkylhydroxylamines such as N,N-diethylhydroxylamine and N-alkyl-N-arylhydroxylamine such as N-ethyl-N-phenylhydroxylamine respectively as short-stopping agents and popcorn polymer inhibitors in processes for preparing synthetic rubber. The popcorn polymer formation is a serious problem encountered in recovering of monomers from such synthetic rubber operations.

U.S. Pat. No. 4,782,105 teaches the use of long chain N,N-dialkylhydroxylamines as stabilizers to prevent the premature gelation of unsaturated elastomer compositions such as styrene/butadiene copolymers or polybutadiene.

U.S. Pat. No. 3,408,422 describes the use of N,N-dialkylhydroxylamines such as N,N-diethylhydroxylamine and N,N-diaralkylhydroxylamines such as N,N-dibenzylhydroxylamine as stabilzers for preventing the premature gelation of unsaturated polyesters.

U.S. Pat. No. 4,798,889 teaches the use of N,N-dialkylhydroxylamines such as N,N-diethylhydroxylamine or N,N-dibenzylhydroxylamine as stabilizers to reduce the thermal polymerization of organosiloxanes substituted by ethylenically unsaturated moieties.

U.S. Pat. Nos. 4,409,408 and 4,434,307 disclose the use of N,N-dibenzylhydroxylamine in combination with an alkylated diphenol (catechol or hydroquinone) as inhibitors to prevent the polymerization of styrene.

The use of stable nitroxyl radicals including those derived from hindered amine moieties has also been disclosed. Typical references are cited below.

Russian Published Application No. 1,139,722 describes the inhibition of styrene and comonomers such as butadiene using 1-oxyl derivatives of hindered amine compounds such as N,N'-bis(1-oxyl-2,2,6,6-tetramethylpiperidin-4-yl)adipamide. The elimination of popcorn polymer and of the clogging of equipment is touted as the result of using such 1-oxyl compounds.

Japanese Sho 60-36501 describes the use of hindered amines and their 1-oxyl and 1-alkyl derivatives as vinyl polymerization inhibitors to improve storage stability of monomers such as acrylate and methacrylate esters.

European Patent Application No. 178,168 and British Patent No. 1,127,127 describe the use of 1-oxyl substituted hindered amine compounds as stabilizers for inhibiting the polymerization of $\alpha,\beta$-ethylenically unsaturated monocarboxylic acids, such as acrylic acid, during its recovery by distillation.

U.S. Pat. No. 4,670,131 teaches the use of 1-oxyl substituted hindered amine compounds as stabilizers for preventing the fouling of equipment for processing organic feed streams containing olefins by inhibiting the polymerization of said olefins.

In a theoretical study of the inhibiting effects of selected hindered amine compounds, Y. Miura et al., Makromol. Chem. 160, 243 (1972) disclose that 1-oxyl-2,2,6,6-tetramethylpiperidin-4-one is highly effective in retarding the onset of the polymerization of styrene and methyl methacrylate. By contrast, the corresponding 1-hydroxy-2,2,6,6-tetramethylpiperidin-4-one is stated to have no effect in delaying the polymerization of styrene and only a weak retarding effect on said polymerization once begun.

U.S. Pat. Nos. 4,668,721 and 4,691,015 disclose the use of 1-hydroxy substituted hindered amine compounds as stabilizers for polyolefin compositions in combination with one or more other stabilizers such as phenolic antioxidants, ultraviolet light absorbers and the like.

None of these references describes or suggests that 1-hydroxy substituted hindered amine compounds are or could possibly be effective inhibitors to prevent the premature polymerization of monomers in either the liquid or vapor phase.

OBJECTS OF THE INVENTION

It is the broad object of the invention to provide monomer compositions inhibited against undesired and premature polymerization by means of small, but effective amounts of selected additives which do not impart undesired color to the monomer compositions.

It is a further object of the invention to provide inhibited monomer compositions which have substantially improved stability relative to compositions inhibited by methods known in the prior art.

It is a further object of the invention to provide a means for short-stopping or retarding polymerization of monomers once polymerization is started.

It is a further object of the invention to provide effective inhibitors for monomers known to be difficult to inhibit such as acrylic acid.

It still a further object of the invention to provide highly effective combinations of inhibitors for said monomers.

DETAIL DISCLOSURE

The invention pertains to a monomer composition, stabilized against premature polymerization, which comprises (a) an ethylenically unsaturated monomer or mixture of monomers, polymerizable by free radical initiation, and (b) an effective amount, sufficient to inhibit the premature polymerization of component (a), of a compound or mixture of compounds of any of formula I to XV, and salts thereof,

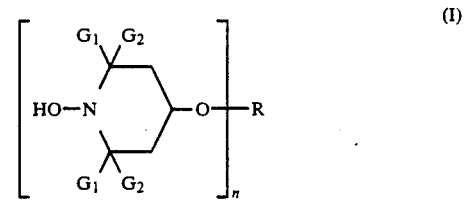

(I)

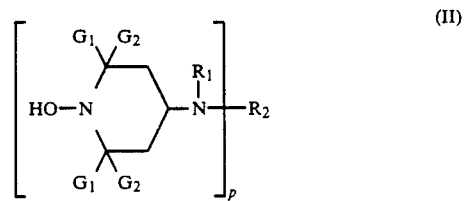

(II)

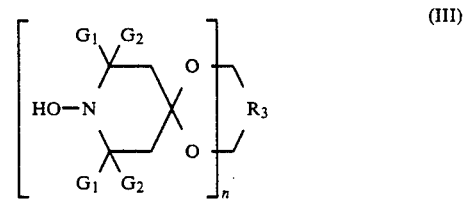

(III)

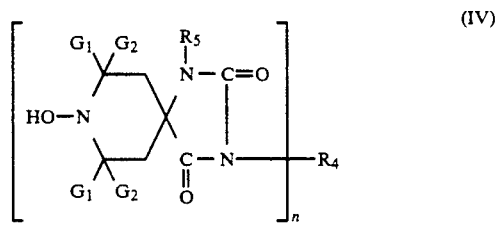

(IV)

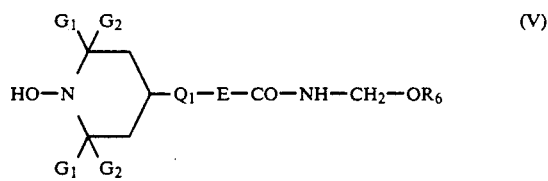

(V)

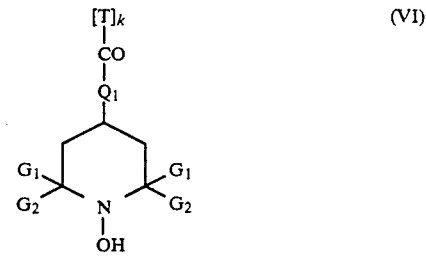

(VI)

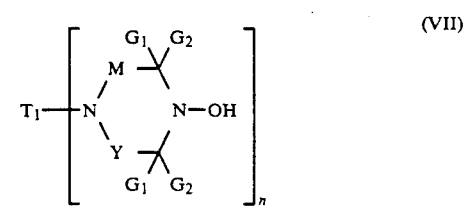

(VII)

-continued

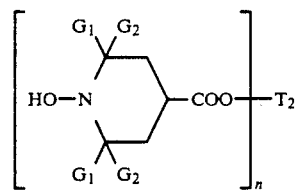 (VIII)

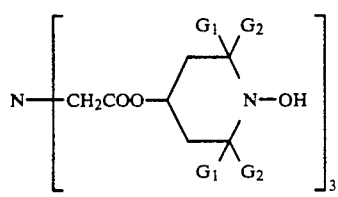 (IX)

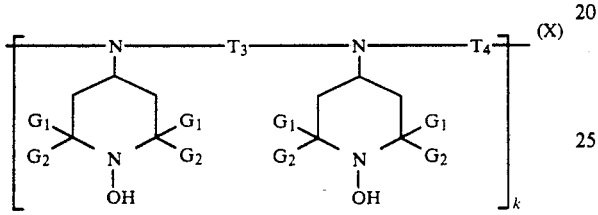 (X)

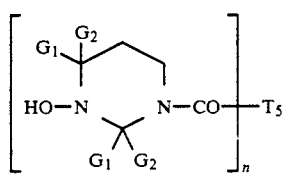 (XI)

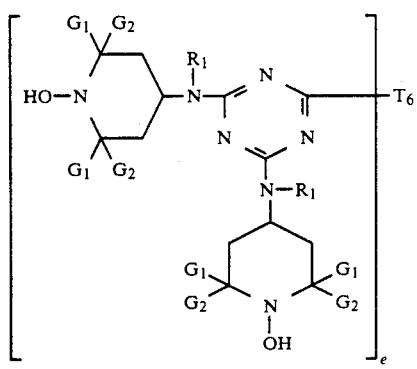 (XII)

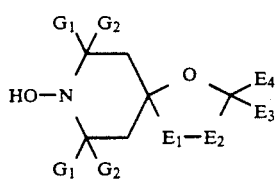 (XIII)

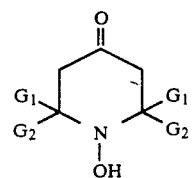 (XIV)

-continued

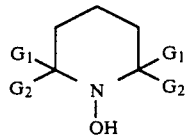 (XV)

wherein $G_1$ and $G_2$ are independently alkyl of 1 to 4 carbon atoms, preferably methyl, or $G_1$ and $G_2$ together are pentamethylene;

n is 1 or 2, when n is 1,

R is hydrogen, $C_1$-$C_{18}$-alkyl optionally interrupted by one or more oxygen atoms, cyanoethyl, benzyl, glycidyl, a monovalent acyl radical of an aliphatic, cycloaliphatic, araliphatic or aromatic acid, or of carbamic acid or of a phosphorus-containing acid, or a monovalent silyl radical, preferably an acyl radical of an aliphatic carboxylic acid having 2 to 18 carbon atoms, of a cycloaliphatic acid having 5 to 12 carbon atoms or of an aromatic carboxylic acid having 7 to 15 carbon atoms, or of carbamic acid; or when n is 2, R is $C_1$-$C_{12}$-alkylene, $C_4$-$C_{12}$-alkenylene, xylene, a divalent acyl radical of an aliphatic, cycloaliphatic, araliphatic or aromatic dicarboxylic acid, or of a dicarbamic acid or of a phosphorus-containing acid, or a bivalent silyl radical, preferably an acyl radical of an aliphatic dicarboxylic acid having 2 to 36 carbon atoms, of a cycloaliphatic or aromatic dicarboxylic acid having 8 to 14 carbon atoms, or of a aromatic dicarbamic acid having 8 to 14 carbon atoms;

p is 1, 2 or 3, $R_1$ is hydrogen, $C_1$-$C_{12}$-alkyl, $C_5$-$C_7$-cycloalkyl, $C_7$-$C_8$-aralkyl, $C_2$-$C_{18}$alkanoyl, $C_3$-$C_5$-alkenoyl or benzoyl;

when p is 1, $R_2$ is hydrogen, $C_1$-$C_{18}$-alkyl, $C_5$-$C_7$-cycloalkyl, $C_2$-$C_8$-alkenyl unsubstituted or substituted by a cyano, carbonyl or carbamide group, or is glycidyl, a group of the formula —$CH_2CH(OH)$—Z or of the formula —CONH—Z wherein Z is hydrogen, methyl or phenyl; or when p is 2, $R_2$ is $C_2$-$C_{12}$-alkylene, $C_6$-$C_{12}$-arylene, eylylene, a —$CH_2CH(OH)CH_2$—O—X—O—$CH_2CH(OH)CH_2$— wherein X is $C_2$-$C_{10}$-alkylene, $C_6$-$C_{15}$-arylene or $C_6$-$C_{12}$-cycloalkylene; or, provided that $R_1$ is not alkanoyl, alkenoyl or benzoyl, $R_2$ can also be a divalent acyl radical of an aliphatic, cycloaliphatic or aromatic dicarboxylic acid or dicarbamic acid, or can be the group —CO—; or $R_1$ and $R_2$ together when p is 1 can be the cyclic acyl radical of an aliphatic or aromatic 1,2- or 1,3-dicarboxylic acid; or $R_2$ is

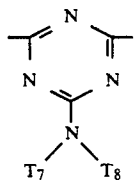

where $T_7$ and $T_8$ are independently hydrogen, alkyl of 1 to 18 carbon atoms, or $T_7$ and $T_8$ together are alkylene of 4 to 6 carbon atoms or 3-oxapentamethylene, preferably $T_7$ and $T_8$ are 3-oxapentamethylene;

when p is 3, $R_2$ is 2,4,6-triazinyl;

when n is 1, $R_3$ is $C_2$-$C_8$-alkylene or hydroxyalkylene or $C_4$-$C_{22}$-acyloxyalkylene; or when n is 2, $R_3$ is $(—CH_2)_2C(CH_2—)_2$;

when n is 1, $R_4$ is hydrogen, $C_1$-$C_{12}$-alkyl, $C_3$-$C_5$-alkenyl, $C_7$-$C_9$-aralkyl, $C_5$-$C_7$-cycloalkyl, $C_2$-$C_4$-hydroxyalkyl, $C_2$-$C_6$-alkoxyalkyl, $C_6$-$C_{10}$-aryl, glycidyl, a group of formula $—(CH_2)_m—COO—Q$ or of the formula $—(CH_2)_m—O—CO—Q$ wherein m is 1 or 2 and Q is $C_1$-$C_4$-alkyl or phenyl; or when n is 2, $R_4$ is $C_2$-$C_{12}$-alkylene, $C_6$-$C_{12}$-arylene, a group $—CH_2CH(OH)CH_2—O—X—O—CH_2CH(OH)CH_2—$ wherein X is $C_2$-$C_{10}$-alkylene, $C_6$-$C_{15}$-arylene or $C_6$-$C_{12}$-cycloalkylene, or a group $—CH_2CH(OZ_1)CH_2—(OCH_2CH(OZ_1)CH_2)_2—$ wherein $Z_1$ is hydrogen, $C_1$-$C_{18}$-alkyl, allyl, benzyl, $C_2$-$C_{12}$-alkanoyl or benzoyl;

$R_5$ is hydrogen, $C_1$-$C_{12}$-alkyl, allyl, benzyl, glycidyl or $C_2$-$C_6$-alkoxyalkyl;

$Q_1$ is $—N(R_7)—$ or $—O—$;

E is $C_1$-$C_3$-alkylene, the group $—CH_2CH(R_8)—O—$ wherein $R_8$ is hydrogen, methyl or phenyl, the group $—(CH_2)_3—NH—$ or a direct bond;

$R_7$ is hydrogen, $C_1$-$C_{18}$-alkyl, $C_5$-$C_7$-cycloalkyl, $C_7$-$C_{12}$-aralkyl, cyanoethyl, $C_6$-$C_{10}$-aryl, the group $—CH_2CH(R_8)—OH$; or a group of the formula

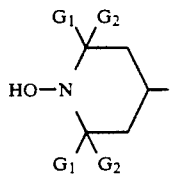

or a group of the formula

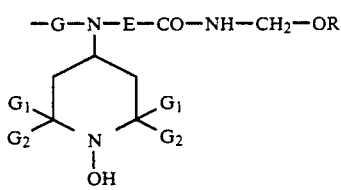

wherein G is $C_2$-$C_6$-alkylene or $C_6$-$C_{12}$-arylene; or $R_7$ is a group $—E—CO—NH—CH_2—OR_6$;

$R_6$ is hydrogen or $C_1$-$C_{18}$-alkyl;

Formula VI denotes a recurring structural unit of a polymer where T is ethylene or 1,2-propylene, or is a repeating structural unit derived from an α-olefin copolymer with an alkyl acrylate or methacrylate, preferably a copolymer of ethylene and ethyl acrylate;

k is 2 to 100;

$T_1$ has the same meaning as $R_2$ when p is 1 or 2;

M and Y are independently methylene or carbonyl, preferably M is methylene and Y is carbonyl, and $T_1$ is ethylene when n is 2;

$T_2$ has the same meaning as $R_4$, and $T_2$ is preferably octamethylene when n is 2, $T_3$ and $T_4$ are independently alkylene of 2 to 12 carbon atoms, of $T_4$ is

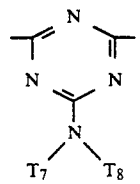

$T_6$ is

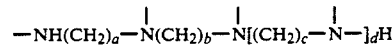

where a, b and c are independently 2 or 3, and d is 0 or 1, preferably a and c are each 3, b is 2 and d is 1;

e is 3 or 4, preferably 4;

$T_5$ is the same as R with the proviso that $T_5$ cannot be hydrogen when n is 1;

$E_1$ and $E_2$, being different, are each oxo or imino, preferably $E_1$ is oxo and $E_2$ is $—N(E_5)—$ where $E_5$ is hydrogen, $C_1$-$C_{12}$-alkyl or alkoxycarbonylalkyl of 4 to 22 carbon atoms;

$E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms; and $E_4$ is hydrogen, alkyl of 1 to 30 carbon atoms, phenyl, naphthyl or phenylalkyl of 7 to 12 carbon atoms; or $E_3$ and $E_4$ together are polymethylene of 4 to 17 carbon atoms, or said polymethylene substituted by up to four alkyl groups of 1 to 4 carbon atoms, preferably methyl.

The monomers of component (a) of this invention are any having at least one carbon-carbon double bond capable of undergoing free radical induced polymerization. Such monomers are well known in commerce and comprise a wide variety of structural types. Typical examples of such monomers are the olefinic hydrocarbons such as styrene, α-methylstyrene and divinylbenzene; dienes such as butadiene and isoprene; halogenated monomers such as vinyl chloride, chloroprene, vinylidene chloride, vinylidene fluoride and vinyl fluoride; unsaturated acids such as acrylic acid, methacrylic acid and crotonic acid; unsaturated esters such as vinyl acetate, alkyl acrylates and alkyl methacrylates such as methyl methacrylate, ethyl acrylate, methyl acrylate, 2-hydroxyethyl acrylate and methacrylate, ethylene bismethacrylate, trimethylolpropane triacrylate, acrylated epoxy resin and polyethylene glycol diacrylate; unsaturated amides such as acrylamide, N,N-dimethylacrylamide, methylene-bisacrylamide and N-vinylpyrrolidone; unsaturated nitrile monomers such as acrylonitrile; and unsaturated ethers such as methyl vinyl ether; and miscellaneous monomers such as the vinyl pyridines, diethyl vinylphosphonate and sodium styrenesulfonate.

The instant invention also pertains to mixtures of said monomers and to resins such as acrylate-terminated polyurethanes and unsaturated polyesters. The common feature making all of these materials relevant to the present invention is the presence of a polymerizable double bond.

Also in the category of monomers are unsaturated oils such as drying oils like linseed oil, where polymerization also incorporates oxygen. There are also adventitious monomers formed in refining processes, for example polymerizable olefinic unsaturation in gasoline, jet fuel, solvents, crude oil and cracked hydrocarbon streams. The common feature of all of these substances is encompassed in the broad term "monomers" and all are contemplated to be within the scope of instant component (a). Polymerization of such materials is often accompanied by autooxidation.

The acrylates, particularly acrylic acid itself, are unusually difficult to inhibit because of their inherent high polymerizability. The instant compounds are shown to be particularly effective in inhibiting acrylic acid from premature polymerization.

Preferably component (a) is a monomer selected from the group consisting of the olefinic hydrocarbons, dienes, halogenated monomers, unsaturated acids, unsaturated esters, unsaturated amides, unsaturated nitriles, unsaturated ethers, acrylated urethanes and unsaturated polyesters and mixtures thereof.

Most preferably the monomer of component (a) is styrene, butadiene, vinyl chloride, acrylic acid, methacrylic acid, vinyl acetate, 2-hydroxyethyl acrylate, 2-hydroxyethyl methacrylate, trimethylolpropane triacrylate, polyethylene glycol diacrylate or methyl methacrylate.

Still more preferably the monomer is styrene, butadiene, acrylic acid or methacrylic acid.

The hydroxylamine derivatives useful in the instant invention are denoted by the various structures of formulas I to XV. Most of these hydroxylamine derivatives are known compounds. The instant hydroxylamine derivatives can be easily prepared from the corresponding hindered amine many of which are commerically available or which can be made by known procedures.

The hydroxylamine derivative may generally be prepared by oxidizing a hindered amine with a peroxy compound such as hydrogen peroxide followed by reduction of the oxyl intermediate formed to the desired hydroxylamine derivative. Such a process is taught in U.S. Pat. No. 4,665,185.

If any of the substitutents are $C_1-C_{12}$-alkyl, they are for example methyl, ethyl, n-propyl, isopropyl, n-butyl, sec-butyl, tert-butyl, n-amyl, tert-amyl, n-hexyl, n-octyl, 2-ethylhexyl, tert-octyl, n-nonyl, n-decyl, n-undecyl or n-dodecyl. As $C_1-C_{18}$-alkyl, R can be the aforementioned groups, and in addition for example n-tridecyl, n-tetradecyl, n-hexadecyl or n-octadecyl.

If R is a monovalent acyl radical of a carboxylic acid, it is for example an acyl radical of acetic acid, stearic acid, salicylic acid, methacrylic acid, acrylic acid, maleic acid, benzoic acid, 2-ethylhexanoic acid or 3,5-ditert-butyl-4-hydroxyhydrocinnamic acid.

If R is a divalent acyl radical of a dicarboxylic acid, it is for example an acyl radical of adipic acid, succinic acid, suberic acid, sebacic acid, o-phthalic acid, butylmalonic acid, dibutylmalonic acid, dibenzylmalonic acid, 3,5-di-tert-butyl-4-hydroxybenzylbutylmalonic acid or bicycloheptene dicarboxylic acid.

If R is a divalent acyl radical of a dicarbamic acid, it is for example an acyl radical of hexamethylenedicarbamic acid or 2,4-toluylenedicarbamic acid.

R is also an acyl radical of a phosphorus-containing acid of the formula

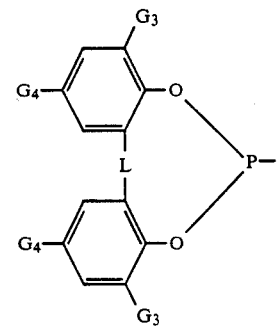

wherein L is a direct bond, methylene or alkylidene of 2 to 6 carbon atoms such as ethylidene, butylidene or amylidene. Preferably L is a direct bond, methylene or ethylidene.

$G_3$ and $G_4$ are independently alkyl of 1 to 4 carbon atoms, preferably methyl or tert-butyl. Most preferably $G_3$ and $G_4$ are each tert-butyl, or $G_3$ is tert-butyl and $G_4$ is methyl.

If any substituents are $C_5-C_7$-cycloalkyl, they are in particular cyclohexyl.

As $C_7-C_8$-aralkyl, $R_1$ is phenethyl and especially benzyl.

As $C_2-C_{18}$-alkanoyl, $R_1$ is for example propionyl, butyryl, octanoyl, lauroyl, hexadecanoyl, octadecanoyl, but especially acetyl; and as $C_3-C_5$-alkenoyl, $R_1$ is in particular acryloyl.

If $R_2$ is $C_2-C_8$-alkenyl unsubstituted or substituted by a cyano, carbonyl or carbamide group, it is for example 1-propenyl, allyl, methallyl, 2-butenyl, 2-pentenyl, 2-hexenyl, 2-octenyl, 2,2-dicyanovinyl, 1-methyl-2-cyano-2-methoxycarbonyl-vinyl or 2,2-diacetylaminovinyl.

When $R_1$ and $R_2$ are together a cyclic acyl radical, they are especially $-CO-(CH_2)_5-$.

If any substituents are $C_2-C_{12}$-alkylene, they are for example ethylene, propylene, 2,2-dimethylpropylene, tetramethylene, hexamethylene, octamethylene, decamethylene or dodecamethylene.

If any substituents are $C_6-C_{15}$-arylene, they are for example o-, m- or p-phenylene, 1,4-naphthylene or 4,4'-diphenylene.

As $C_6-C_{12}$-cycloalkylene, X is especially cyclohexylene.

If $R_3$ is $C_2-C_8$-alkylene or hydroxyalkylene, it is for example ethylene, 1-methyl-ethylene, propylene, 2-ethylpropylene or 2-ethyl-2-hydroxymethylpropylene.

As $C_4$-$C_{22}$acyloxyalkylene, $R_3$ is for example 2-ethyl-2-acetoxymethyl-propylene.

If any substituents are $C_2$-$C_6$-alkoxyalkyl, they are example methoxymethyl, ethoxymethyl, propoxymethyl, tert-butoxymethyl, ethoxyethyl, ethoxypropyl, n-butoxyethyl, tert-butoxyethyl, isopropoxyethyl or propoxypropyl.

If $R_4$ is $C_3$-$C_5$-alkenyl, it is for example 1-propenyl, allyl, methallyl, 2-butenyl or 2-pentenyl.

As $C_7$-$C_9$-aralkyl, $R_4$ is phenethyl or especially benzyl; and as $C_5$-$C_7$-cyclohexyl is especially cyclohexyl.

If $R_4$ is $C_2$-$C_4$-hydroxyalkyl, it is for example 2-hydroxyethyl, 2-hydroxypropyl, 3-hydroxypropyl, 2-hydroxybutyl or 4-hydroxybutyl.

As $C_6$-$C_{10}$-aryl, $R_4$ is in particular phenyl or α-or β-naphthyl which is unsubstituted or substituted by halogen or $C_1$-$C_4$-alkyl.

If $R_4$ is $C_2$-$C_{12}$-alkylene, it is for example ethylene, propylene, 2,2-dimethylpropylene, tetramethylene, hexamethylene, octamethylene, decamethylene or dodecamethylene.

If $R_4$ is $C_6$-$C_{12}$-arylene, it is for example o-, m-or p-phenylene, 1,4-naphthylene or 4,4'-diphenylene.

If $Z_1$ is $C_2$-$C_{12}$-alkanoyl, it is for example propionyl, butyryl, octanoyl, dodecanoyl or preferably acetyl.

As $C_5$-$C_7$-cycloalkyl, $R_7$ is particularly cyclohexyl.

As $C_6$-$C_{10}$-aryl, $R_7$ is particularly phenyl or α-or β-naphthyl which is unsubstituted or substituted with halogen or $C_1$-$C_4$-alkyl.

As $C_1$-$C_3$-alkylene, E is for example methylene, ethylene or propylene.

As $C_2$-$C_6$-alkylene, G is for example ethylene, propylene, 2,2-dimethylpropylene, tetramethylene or hexamethylene; and as $C_6$-$C_{12}$-arylene, G is o-, m- or p-phenylene, 1,4-naphthylene or 4,4'-diphenylene.

An effective inhibiting amount of an instant compound of this invention needed to retard or prevent premature free radical induced polymerization of a monomer or monomer mixture is in the range of from 1 to 10,000 ppm, based on the total monomer composition, with the preferred range being 5 to 2000 ppm and the most preferred range being 50 to 1000 ppm. The lower amounts would be used where the degree of inhibition required is not great such as when the monomers are to be used promptly, or which will be stored refrigerated, or which are inherently less prone to polymerize readily such as monomers with internal double bonds. The higher amounts of inhibitor would be used where the monomer is to be stored for prolonged periods of time, especially under relatively warm conditions or where contamination is likely, or where exposure to photoinitiation is likely, or where the monomer is especially prone to rapid polymerization with little provocation such as with the acrylates and acrylic acid. Those skilled in the art of vinyl polymerization are well aware of the relative polymerizability of monomers and of their relative stabilities.

The stabilized compositions of this invention are distinguished by their lack of color.

The compositions of the instant invention may also contain additional inhibitors, such as hydroquinone, the monomethyl ether of hydroquinone, phenothiazine (these three often being required by monomer specifications) or catechol, tert-butylated hydroquinones or catechols, other alkylated phenols, nitrosophenols, nitrosophenylhydroxylamines, alkylated phenothiazines, sulfur and hindered cyclic amines or their corresponding oxyl derivatives.

The inhibited compositions may also contain metal deactivators and UV absorbers to improve light stability; or stabilizers such as amines to retard acid-catalyzed degradation; or thermal or photoinitiators; and other conventional additives.

The process of the instant invention involves simply dissolving an effective inhibiting amount of the inhibitor in the monomer prior to exposure of the latter to conditions where the premature, undesired free radical initiated polymerization might occur.

When it is desired to subject the inhibited monomer to polymerization, the inhibitor can either be removed or overridden by sufficient polymerization initiator. Removal can be accomplished by distillation, absorption or washing with an acidic solution. It is possible to remove the instant 1-hydroxy derivatives while leaving the phenolic antioxidants in the monomer by use of acid ion exchange resins. The polymerization inhibiting action of the instant compounds can be overridden by use of sufficient free radical initiator, actinic light irradiation, electron beam exposure or other polymerization initiating means.

The instant invention also pertains to a process which comprises adding 10 to 500 ppm of at least one compound of formula I to XVII to a continuous fluid feed stream to deactivate the autocatalytic polymerization, in any part of the continuous process equipment, such as reactor, reboiler, distillation column, etc., of any ethylenically unsaturated monomer present in the feed stream, and further adding to said feed stream an additional 10 ppb to 500 ppm of at least one compound of formula I to XVII as a makeup additive to maintain the desired concentration of said compound in the fluid feed stream being processed.

The following examples are presented for the purpose of illustration only and are not to be construed as limiting the instant invention in any manner whatsoever.

EXAMPLE 1

Trimethylolpropane triacrylate is extracted with cold dilute aqueous alkali to remove the monomethyl ether of hydroquinone which is present as an inhibitor. To 25 g samples of the uninhibited monomer is added 20 ppm of the test inhibitor and the sample is then placed in a 1 oz (28 ml) amber bottle in an oven kept at 100° C. The time required for polymerization as visually observed by the formation of gelled lumps or solid matter to occur is a measure of the effectiveness of the test inhibitor.

| Inhibitor* | Hours to Failure (= Gelation) |
|---|---|
| None | 36 |
| Compound A | 211 |
| Compound B | 180 |

*Compound A is N-(1-hydroxy-2,2,6,6-tetramethylpiperidin-4-yl)caprolactam.
Compound B is Bis(1-hydroxy-2,2,6,6-tetramethylpiperidin-4-yl) sebacate.

EXAMPLE 2

The effect of the presence of the test inhibitor on the yellowness of a cured acrylic resin is determined by measuring yellowness index (YI). To a mixture of 50% by weight of epoxy acrylate (CELRAD 3700, Celanese), 19% by weight of trimethylolpropane triacrylate, 19% by weight of ethoxylated trimethylolpropane triacrylate, 10% by weight of polyethylene glycol (200) diacrylate and 2% by weight of hydroxycyclohexyl phenyl ketone photoinitiator is added 20 ppm of the test inhibitor. The mixture is coated onto paper and passed at 10 ft/min (3.05 m/min) under a 200 watt/in medium pressure mercury arc lamp in a PPG UV Processor at full power.

The cure is evaluated by a standard surface hardness test method and the presence of the test inhibitor is found to have no adverse effect on the rate of cure or the hardness of the cured resin.

The yellowness index is then determined bu means of an XL-10A Colorimeter (Gardner Laboratory) using a normal beam and a 1.5 inch (3.8 cm) orifice. A YI value is obtained immediately after curing is complete and then again after the cured resin is exposed to an accelerated weathering device for 24 hours to determine the light stability of the cured resin in a simulated office environment.

| Inhibitor* | Yellowness Index | |
|---|---|---|
| | After Cure | After Weathering |
| None | 4.2 | 14 |
| Compound A | 4.3 | 11.6 |
| Compound B | 4.6 | 11.5 |

*Compound A and Compound B are named in Example 1.

These data indicate that the presence of the test inhibitor improves the resistance of the cured resin to yellowing under simulated office lighting conditions.

EXAMPLE 3

Liquid Phase Inhibition

Test inhibitors are added at the 10 ppm and at the 100 ppm level into a variety of unihibited monomers. The monomer containing the test inhibitor is then held at 80° C. in sealed bottles till polymerization of the monomer is observed visually. The time in hours till polymerization occurs is a measure of the effectiveness of the test compound as an inhibitor. Control tests are run with each monomer where the inhibitor is the monomethyl ether of hydroquinone.

| Inhibitor* (ppm) | Hours to Failure (= Gelation) | | | | | |
|---|---|---|---|---|---|---|
| | Styr | HEMA | MMA | AA | HEA | VAc (at 60° C.) |
| None | 48 | 55 | 81 | 48 | 304 | 330 |
| MEHQ (50) | 48 | 90 | 760 | 48 | 330 | >1100 |
| MEHQ (100) | 48 | 90 | 430 | 128 | 430 | 250 |
| MEHQ (500) | 90 | 90 | 4524 | 1936 | 4289 | >1100 |
| Compound A (10) | 48 | 90 | 120 | 164 | 2100 | 356 |
| Compound A (100) | 90 | 164 | 352 | 1000 | >10000 | >1100 |
| Compound B (10) | 48 | 90 | 128 | 250 | 1984 | 352 |
| Compound B (100) | 90 | 90 | 7150 | 1200 | 7700 | >1100 |

*Compound A and Compound B are named in Example 1.
Styr is styrene.
HEMA is 2-hydroxyethyl methacrylate.
MMA is methyl methacrylate.
AA is acrylic acid.
HEA is 2-hydroxyethyl acrylate.
VAc is vinyl acetate.

In all the monomers except styrene, 10 ppm of Compound A or Compound B provides significantly greater polymerization inhibition compared to the unihibited controls. In all the monomers save acrylic acid, 100 ppm of Compound B provides equal or greater polymerization inhibition than does 500 ppm of the monomethyl ether of hydroquinone.

EXAMPLE 4

Using the general method described in Example 3, the relative effectiveness of N-hydroxypiperidines compared to the corresponding N-oxylpiperidines is measured using methyl methacrylate monomer and 100 ppm of test inhibitor with the inhibited monomer being placed in sealed bottles at 80° C. The time in hours till gelation is visually observed is taken as a measure of the inhibition efficacy of the test compound.

| Inhibitor* | Hours to Failure (= Gelation) | |
|---|---|---|
| | N-hydroxy | N-oxyl |
| Compound A | >6900 | — |
| Compound C | — | 1400 |
| Compound B | >2700 | — |
| Compound D | — | 3060 |
| Compound E | 3190 | — |
| Compound F | — | 418 |
| Compound G | >8300 | — |
| Compound H | — | 5600 |
| Compound I | >8300 | — |
| Compound J | — | 2400 |

*Compound A is N-(1-hydroxy-2,2,6,6-tetramethylpiperidin-4-yl)caprolactam.
Compound C is N-(1-oxyl-2,2,6,6-tetramethylpiperidin-4-yl)caprolactam.
Compound B is bis(1-hydroxy-2,2,6,6-tetramethylpiperidin-4-yl) sebacate.
Compound D is bis(1-oxyl-2,2,6,6-tetramethylpiperidin-4-yl) sebacate.
Compound E is 1-hydroxy-2,2,6,6-tetramethylpiperidin-4-yl benzoate.
Compound F is 1-oxyl-2,2,6,6-tetramethylpiperidin-4-yl benzoate.
Compound G is 1-hydroxy-2,2,6,6-tetramethylpiperidin-4-yl acrylate.
Compound H is 1-oxyl-2,2,6,6-tetramethylpiperidin-4-yl acrylate.
Compound I is 1,4-dihydroxy-2,2,6,6-tetramethylpiperidine.
Compound J is 1-oxyl-4-hydroxy-2,2,6,6-tetramethylpiperidine.

The data given in the table above show that the 1-hydroxy substituted piperidines are clearly superior in polymerization inhibition efficacy compared to the corresponding 1-oxyl compounds. Additionally, the 1-hydroxy compounds are essentially colorless while the 1-oxyl compounds are highly colored, usually red.

EXAMPLE 5

N,N-Dialkylhydroxylamines are known as monomer stabilizers Using the general procedure of Example 3 with commercial methyl methacrylate (MMA), with 10 ppm of monomethyl ether of hydroquinone present as an inhibitor, 100 ppm of test inhibitors are added to 25 g portions of the MMA in 1 ounce (28 ml) bottles. The samples are placed in an oven at 80° C. and the time required for polymerization or gelation to occur is visually observed.

| Inhibitior* | Hours to Failure (= Gelation) |
|---|---|
| DEHA | 34 |
| DBHA | 155 |
| Compound G | 1962 |
| Compound K | 370 |
| Compound L | 1400 |
| Compound M | 1000 |
| Compound N | 1400 |
| Compound O | 370 |
| Compound P | 1255 |
| Compound Q | 250 |
| Compound R | 1335 |
| Compound S | 850 |

| Inhibitior* | Hours to Failure (= Gelation) |
|---|---|
| Compound T | 880 |

*DEHA is N,N-diethylhydroxylamine
DBHA is N,N-dibenzylhydroxylamine.
Compound G is 1-hydroxy-2,2,6,6-tetramethylpiperidin-4-yl acrylate.
Compound K is 1-hydroxy-2,2,6,6-tetramethylpiperidin-4-yl 3,5-di-tert-butyl-4-hydroxybenzoate.
Compound L is 4,4'-ethylenebis(1-hydroxy-2,2,6,6-tetramethylpiperazin-3-one).
Compound M is 1-hydroxy-2,2,6,6-tetramethylpiperidin-4-yl stearate.
Compound N is bis(1-hydroxy-2,2,6,6-tetramethylpiperidin-4-yl) o-phthalate.
Compound O is bis(1-hydroxy-2,2,6,6-tetramethylpiperidin-4-yl) 3,5-di-tert-butyl-4-hydroxybenzyl-butyl-malonate.
Compound P is bis(1-hydroxy-2,2,6,6-tetramethylpiperidin-4-yl) n-butylmalonate.
Compound Q is 2,10-di-tert-butyl-4,8-dimethyl-6-(1-hydroxy-2,2,6,6-tetramethylpiperidin-4-yloxy)-dibenzo[d,g][1,3,2]-dioxaphosphocin.
Compound R is 1-hydroxy-2,2,6,6-tetramethylpiperidin-4-yl 2-ethylhexanoate.
Compound S is the dinonylnaphthalene disulfonic salt of bis(1-hydroxy-2,2,6,6-tetramethylpiperidin-4-yl) sebacate.
Compound T is the phosphorous acid salt of bis(1-hydroxy-2,2,6,6-tetramethylpiperidin-4-yl) sebacate.

Each of these test inhibitors provides excellent polymerization inhibition protection to the methyl methacrylate monomer.

These data show that the instant inhibitors are far more effective than the known inhibitors N,N-diethylhydroxylamine and N,N-dibenzylhydroxylamine.

EXAMPLE 6

To assess the effect of the instant test inhibitors on color development in the inhibited monomer, 3 ml portions of methyl methacrylate containing 100 ppm of the test inhibitor are placed in clear sealable test tubes. The tubes are sealed and then heated at 80° C. for 100 hours while protected from light. The tubes are then placed in a colorimeter and the yellowness index (YI) values of the samples are measured. The higher is the YI value the yellower and more discolored is the sample.

| Inhibitor* | Yellowness Index after 100 Hours |
|---|---|
| All samples | 33.9 (before heating at 80° C.) |
| none | 42.4 (gelled in 24 hours) |
| hydroquinone | 59.3 |
| MEHQ | 92.9 |
| phenothiazine | 94.4 (turned pink) |
| Compound B | 41.7 |

*MEHQ is monomethyl ether of hydroquinone.
Compound B is bis(1-hydroxy-2,2,6,6-tetramethylpiperidin-4-yl) sebacate.

The instant inhibitor causes much less yellowing or discoloration than prior art inhibitors.

EXAMPLES 7–14

Vapor Phase Inhibition

To 105 g (100 ml) of acrylic acid is added 1000 ppm by weight of phenothiazine as a non-volatile pot stabilizer. This acrylic acid solution is mixed well and then added to a resin kettle whose weight is known which is fitted with a reflux condenser and nitrogen inlet tube. A stream of nitrogen at 250 ml/min is used to flush the kettle for 15 minutes. The kettle containing the acrylic acid is then immersed into a 6-liter oil bath such that the top of the acrylic acid solution is approximately two inches (5.08 cm) below the level of the oil surface. The kettle and its contents are heated at 150° C. for 100 minutes causing the acrylic acid to reflux. White insoluble polymer, commonly called popcorn polymer, is observed to grow on the walls in the reflux region of the apparatus. The kettle is removed from the oil bath and cleaned free of oil. The kettle is rinsed with hexane to remove the acrylic acid monomer and to leave the polymer. The kettle and polymer are dried and weighed to determine the total amount of polymer collected on the inside wall of the kettle. In this case 78 grams of polymer are obtained.

In like manner other monomers and other inhibitors are tested using the general procedure of Example 8. The results of these experiments are given in the table below.

| Example | Inhibitor*(ppm) | Monomer**(100 ml) | Polymer Formed grams |
|---|---|---|---|
| 7 | phenothiazine (1000) | acrylic acid | 78 |
| 8 | DEHA (100) | acrylic acid | 66 |
| 9 | Compound E (100) | acrylic acid | 33 |
| 10 | Compound U (100) | acrylic acid | 44 |
| 11 | Compound B (100) | acrylic acid | 56 |
| 12 | Compound U (100) | MMA | none |
| 13 | Compound U (100) | HEMA | none |
| 14 | Compound U (100) | HEA | none |

*DEHA is N,N-diethylhydroxylamine.
Compound B is bis(1-hydroxy-2,2,6,6-tetramethylpiperidin-4-yl) sebacate.
Compound E is 1-hydroxy-2,2,6,6-tetramethylpiperidin-4-yl benzoate.
Compound U is 1-hydroxy-2,2,6,6-tetramethylpiperidin-4-one.
**MMA is methyl methacrylate.
HEMA is 2-hydroxyethyl methacrylate.
HEA is 2-hydroxyethyl acrylate.

These data show that the instant compounds are effective in preventing the formation of popcorn polymer in the vapor phase.

What is claimed is:

1. A process for preventing the premature polymerization of (a) an ethylenically unsaturated monomer or mixture of monomers, polymerizable by free radical initiation, which comprises
adding to said monomer (a) an effective amount, sufficient to inhibit the premature polymerization of monomer (a), of (b) a compound or mixture of compounds selected from the group consisting of the compounds of formulas I, II, V, VI, VIII and X, and N-(1-hydroxy-2,2,6,6-tetramethylpiperidin-4-yl)caprolactam and salts thereof,

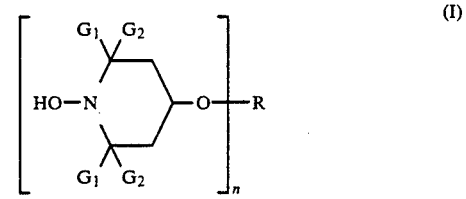

(I)

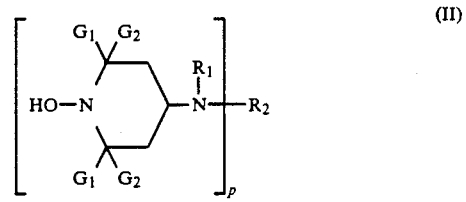

(II)

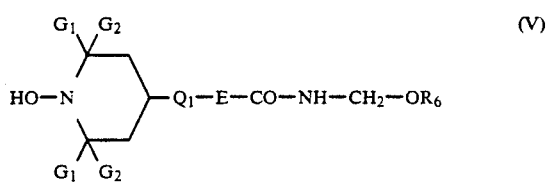

(V)

-continued

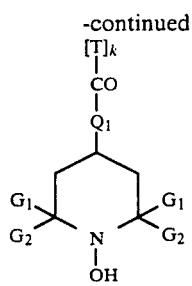
(VI)

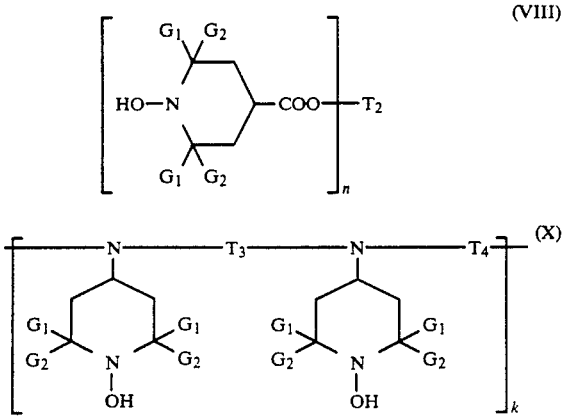
(VIII)

(X)

wherein
G$_1$ and G$_2$ are independently alkyl of 1 to 4 carbon atoms, or G$_1$ and G$_2$ together are pentamethylene;
n is 1 or 2,
when n is 1,
R is C$_1$–C$_{18}$-alkyl optionally interrupted by one or more oxygen atoms, cyanoethyl, benzyl, glycidyl, a monovalent acyl radical of an aliphatic, cycloaliphatic, araliphatic or aromatic acid, or of carbamic acid or of a phosphorus-containing acid, or a monovalent silyl radical; or
when n is 2,
R is C$_1$–C$_{12}$-alkylene, C$_4$–C$_{12}$-alkenylene, xylylene, a divalent acyl radical of an aliphatic, cycloaliphatic, araliphatic or aromatic dicarboxylic acid, or of a dicarbamic acid or of a phosphorus-containing acid, or a bivalent silyl radical;
p is 1, 2 or 3,
R$_1$ is hydrogen, C$_1$–C$_{12}$-alkyl, C$_5$–C$_7$-cycloalkyl, C$_7$–C$_8$-aralkyl, C$_2$–C$_{18}$-alkanoyl, C$_3$–C$_5$-alkenoyl or benzoyl;
when p is 1,
R$_2$ is hydrogen, C$_1$–C$_{18}$-alkyl, C$_5$–C$_7$-cycloalkyl, C$_2$–C$_8$-alkenyl unsubstituted or substituted by a cyano, carbonyl or carbamide group, or is glycidyl, a group of the formula —CH$_2$CH(OH)—Z or of the formula —CONH—Z wherein Z is hydrogen, methyl or phenyl; or
when p is 2,
R$_2$ is C$_2$–C$_{12}$-alkylene, C$_6$–C$_{12}$-arylene, xylylene, a —CH$_2$CH(OH)CH$_2$—O—X—O—CH$_2$CH(OH)CH$_2$— wherein X is C$_2$–C$_{10}$-alkylene, C$_6$–C$_{15}$-arylene or C$_6$–C$_{12}$-cycloalkylene; or, provided that R$_1$ is not alkanoyl, alkenoyl or benzoyl, R$_2$ can also be a divalent acyl radical of an aliphatic, cycloaliphatic or aromatic dicarboxylic acid or dicarbamic acid, or can be the group —CO—; or R$_1$ and R$_2$ together when p is 1 can be the cyclic acyl radical of an aliphatic or aromatic 1,2- or 1,3-dicarboxylic acid; or
R$_2$ is

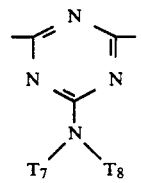

where T$_7$ and T$_8$ are independently hydrogen, alkyl of 1 to 18 carbon atoms, or T$_7$ and T$_8$ together are alkylene of 4 to 6 carbon atoms or 3-oxapentamethylene, preferably T$_7$ and T$_8$ are 3-oxapentamethylene;
when p is 3,
R$_2$ is 2,4,6-triazinyl;
Q$_1$ is —N(R$_7$)— or —O—;
E is C$_1$–C$_3$-alkylene, the group —CH$_2$CH(R$_8$)—O— wherein R$_8$ is hydrogen, methyl or phenyl, the group —(CH$_2$)$_3$—NH— or a direct bond;
R$_7$ is hydrogen, C$_1$–C$_{18}$-alkyl, C$_5$–C$_7$-cycloalkyl, C$_7$–C$_{12}$-aralkyl, cyanoethyl, C$_6$–C$_{10}$-aryl, the group —CH$_2$CH(R$_8$)—OH; or a group of the formula

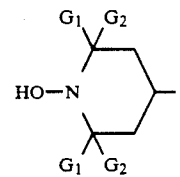

or a group of the formula

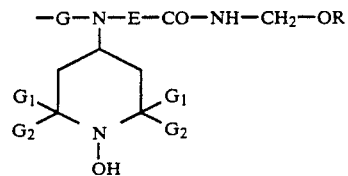

wherein G is C$_2$–C$_6$-alkylene or C$_6$–C$_{12}$-arylene; or
R$_7$ is a group —E—CO—NH—CH$_2$—OR$_6$;
R$_6$ is hydrogen or C$_1$–C$_{18}$-alkyl;
formula VI denotes a recurring structural unit of a polymer where T is ethylene or 1,2-propylene, or is a repeating structural unit derived from an α-olefin copolymer with an alkyl acrylate or methacrylate;
k is 2 to 100;
when n is 1,
T$_2$ is hydrogen, C$_1$–C$_{12}$-alkyl, C$_3$–C$_5$-alkenyl, C$_7$–C$_9$-aralkyl, C$_5$–C$_7$-cycloalkyl, C$_2$–C$_4$-hydroxyalkyl, C$_2$–C$_6$-alkoxyalkyl, C$_6$–C$_{10}$-aryl, glycidyl, a group of formula —(CH$_2$)$_m$—COO—Q or of the formula —(CH$_2$)$_m$—O—CO—Q wherein m is 1 or 2 and Q is C$_1$–C$_4$-alkyl or phenyl; or
when n is 2,
T$_2$ is C$_2$–C$_{12}$-alkylene, C$_6$–C$_{12}$-arylene, a group —CH$_2$CH(OH)CH$_2$—O—X—O—CH$_2$CH(OH)CH$_2$— wherein X is C$_2$–C$_{10}$-alkylene, C$_6$–C$_{15}$-arylene or C$_6$–C$_{12}$-cycloalkylene, or a group —CH$_2$C-

H(OZ$_1$)CH$_2$—(OCH$_2$CH(OZ$_1$)CH$_2$)$_2$— wherein Z$_1$ is hydrogen, C$_1$–C$_{18}$-alkyl, allyl, benzyl, C$_2$–C$_{12}$-alkanoyl or benzoyl;

T$_3$ and T$_4$ are independently alkylene of 2 to 12 carbon atoms, of T$_4$ is

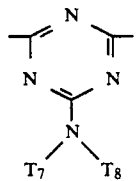

2. A process for preventing the fouling of processing equipment including reactors, pipes, stills, distillation columns, cracking towers and heat transfer surfaces during the processing of a monomer polymerizable by free radical initiation which comprises
adding to said monomer, before processing is begun, an effective amount of a compound (b) as described in claim 1.

3. A process which comprises
adding 10 to 500 ppm of at least one compound (b), as described in claim 1, of formulas I, II, V, VI, VIII and X, or N-(1-hydroxy-2,2,6,6-tetramethylpiperidin-4-yl)caprolactam and salts thereof, to a continuous fluid feed stream to deactivate the autocatalytic polymerization, in any part of the continuous process equipment, of any ethylenically unsaturated monomer present in the feed stream, and
further adding to said feed stream an additional 10 ppb to 500 ppm of at least one compound (b) as a makeup additive to maintain the desired concentration of said compound in the fluid feed stream being processed.

4. A process according to claim 1 wherein the effective amount of compound (b) is 1 to 10,000 ppm, based on the total monomer composition.

5. A process according to claim 4 wherein the effective amount of compound (b) is 5 to 2000 ppm.

6. A process according to claim 5 wherein the effective amount of compound (b) is 50 to 1000 ppm.

7. A process according to claim 1 wherein monomer (a) is a monomer selected from the group consisting of the olefinic hydrocarbons, dienes, halogenated monomers, unsaturated acids, unsaturated esters, unsaturated amides, unsaturated nitriles, unsaturated ethers, acrylated urethanes and unsaturated polyesters and mixtures thereof.

8. A process according to claim 7 wherein the monomer (a) is styrene, butadiene, vinyl chloride, acrylic acid, methacrylic acid, vinyl acetate, 2-hydroxyethyl acrylate, 2-hydroxyethyl methacrylate, trimethylolpropane triacrylate, polyethylene glycol diacrylate or methyl methacrylate.

9. A process according to claim 8 wherein the monomer (a) is styrene, butadiene, acrylic acid or methacrylic acid.

10. A process according to claim 1 wherein compound (b) is formula I or II.

11. A process according to claim 10 wherein compound (b) is of formula I.

12. A process according to claim 1 wherein compound (b) is selected from the group consisting of
N-(1-hydroxy-2,2,6,6-tetramethylpiperidin-4-yl)caprolactam;
bis(1-hydroxy-2,2,6,6-tetramethylpiperidin-4-yl)sebacate;
1-hydroxy-2,2,6,6-tetramethylpiperidin-4-yl benzoate;
1-hydroxy-2,2,6,6-tetramethylpiperidin-4-yl acrylate;
1-hydroxy-2,2,6,6-tetramethylpiperidin-4-yl 3,5-di-tert-butyl-4-hydroxybenzoate;
1-hydroxy-2,2,6,6-tetramethylpiperidin-4-yl stearate;
bis(1-hydroxy-2,2,6,6-tetramethylpiperidin-4-yl) o-phthalate;
bis(1-hydroxy-2,2,6,6-tetramethylpiperidin-4-yl) 3,5-di-tert-butyl-4-hydroxybenzylbutyl-malonate;
bis(1-hydroxy-2,2,6,6-tetramethylpiperidin-4-yl) n-butylmalonate;
2,10-di-tert-butyl-4,8-dimethyl-6-(1-hydroxy-2,2,6,6-tetramethyl-piperidin-4-yloxy)dibenzo[d,g][1,3,2]dioxaphosphocin;
1-hydroxy-2,2,6,6-tetramethylpiperidin-4-yl 2-ethylhexanoate;
dinonylnaphthalene disulfonic salt of bis(1-hydroxy-2,2,6,6-tetramethylpiperidin-4-yl) sebacate; and
the phosphorus acid salt of bis(1-hydroxy-2,2,6,6-tetramethylpiperidin-4-yl) sebacate.

* * * * *

UNITED STATES PATENT AND TRADEMARK OFFICE
CERTIFICATE OF CORRECTION

PATENT NO. : 5,290,888

DATED : March 1, 1994

INVENTOR(S) : Leslie R. Gatechair, et al.

It is certified that error appears in the above-identified patent and that said Letters Patent is hereby corrected as shown below:

On the cover page, Item [75], should read--

Leslie R. Gatechair, Katonah, N.Y.; James L. Hyun, Danbury, CT; Peter J. Schirmann, Fairfield, CT; Harry Evers, Clinton Corners, N.Y. --.

Signed and Sealed this

Twenty-eighth Day of June, 1994

Attest:

BRUCE LEHMAN

*Attesting Officer*     *Commissioner of Patents and Trademarks*